United States Patent [19]

Sugarman

[11] 4,311,138
[45] Jan. 19, 1982

[54] ILLUMINATED HYPODERMIC NEEDLE

[76] Inventor: Edward D. Sugarman, 6726 Gleason Pl., Fayetteville, N.Y. 13066

[21] Appl. No.: 128,826

[22] Filed: Mar. 10, 1980

[51] Int. Cl.³ .............................................. A61M 5/00
[52] U.S. Cl. ................................. 128/214.4; 128/397; 128/215
[58] Field of Search ..................... 128/214.4, 215, 634, 128/348, 397, 398, 214.2, 214 R; 433/29

[56] References Cited

U.S. PATENT DOCUMENTS

| | | | |
|---|---|---|---|
| 3,068,739 | 12/1962 | Hicks, Jr. et al. | 128/397X |
| 3,094,122 | 6/1963 | Gauthier et al. | 128/214.4 |
| 3,693,623 | 9/1972 | Harte et al. | 128/398 X |
| 3,866,599 | 2/1975 | Johnson | 128/634 |

FOREIGN PATENT DOCUMENTS 476573 12/1952 Italy ..................... 128/397

Primary Examiner—Robert Peshock
Assistant Examiner—Mickey Yu
Attorney, Agent, or Firm—Bruns & Jenney

[57] ABSTRACT

A hypodermic needle adapted to emit light from its distal end to facilitate venopuncture under subdued lighting conditions. The needle is used in conjunction with a portable light source, such as a battery handle and lamp, and includes a bundle of optical fibers that transmits light from the lamp to the distal end of the needle. A flexible catheter is releasably mounted on the needle and is adapted to be inserted in the vein after the needle has punctured same and thereafter the needle can be withdrawn from the catheter.

4 Claims, 5 Drawing Figures

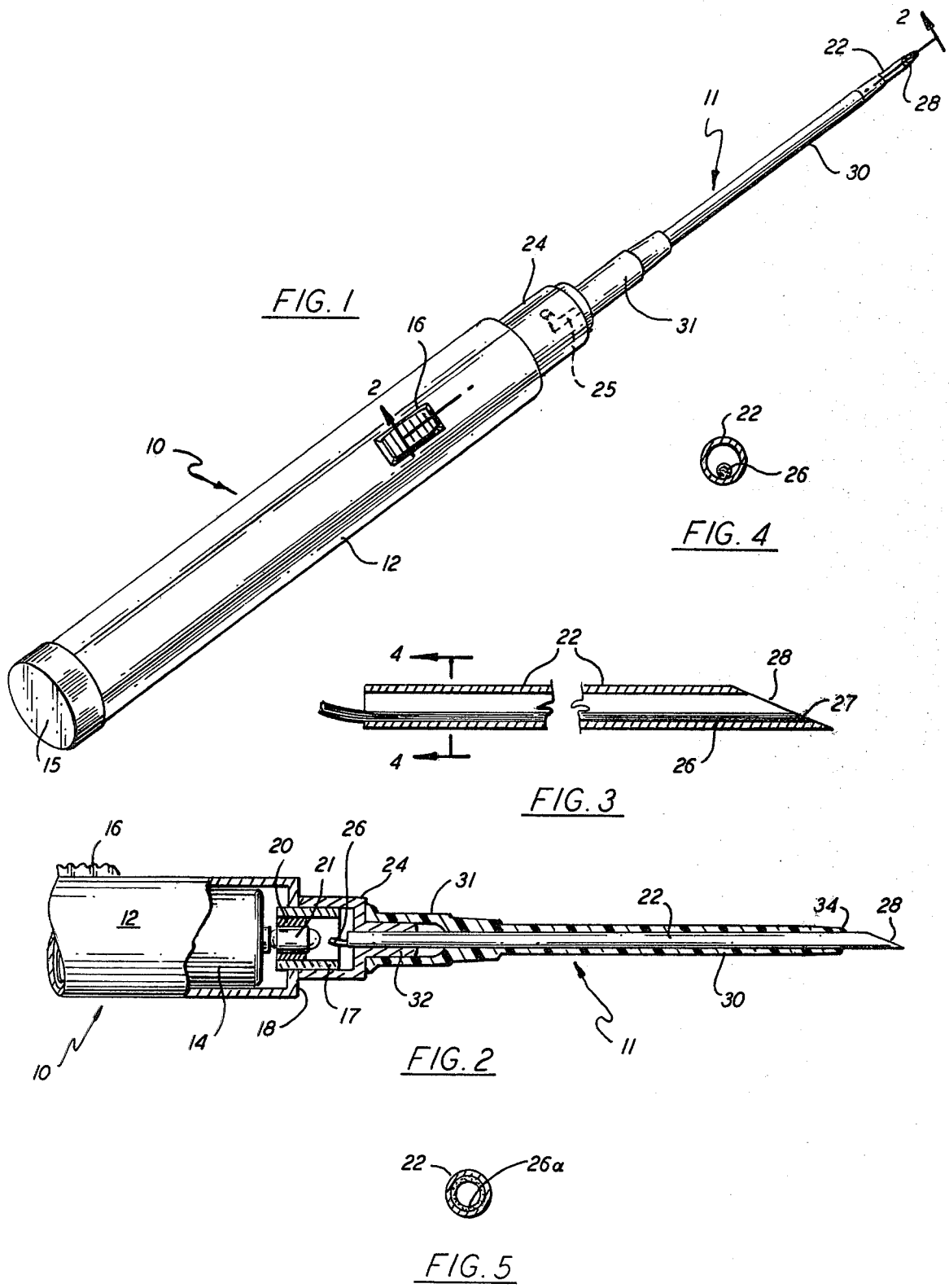

ILLUMINATED HYPODERMIC NEEDLE

BACKGROUND OF THE INVENTION

This invention relates generally to medical equipment, and has particular reference to a novel illuminated hypodermic needle.

One of the earliest procedures used in the treatment of acutely injured or ill patients is that of establishing an intervenous route for the administration of fluids, blood and medications. At times, this procedure is also used to monitor the central venous pressure and other conditions within the body. The procedure requires a hypodermic needle to puncture the wall of a vein and after puncture by the needle, a catheter is usually inserted in the vein and taped in position. The catheter eliminates the possibility of damage to the vein by the needle, and also allows greater patient mobility than is permitted by a rigid needle.

Normally, there is little difficulty in carrying out the above described procedure but in certain problem situations, such as when the light is poor or the patient is elderly or in a state of shock, difficulty may be encountered in locating the vein with the needle point. There is therefore a need for a hypodermic needle having an illuminated point whereby venopuncture is facilitated.

SUMMARY OF THE INVENTION

The hypodermic needle of the present invention provides means for illuminating the needle point or distal end, and this enables the person performing the venopuncture to accurately guide the needle point into the lumen of the vein. The veins most often used for venopuncture lie in the subcutaneous areas of the body and because of the structure of the venous walls and fact that they are filled with blood, the veins have a different density than the surrounding subcutaneous tissues. Due to this density difference, the vein appears darker by contrast and can be more easily located and penetrated using the illuminated needle of the invention.

The illuminated hypodermic needle is particularly adapted for use with a portable light source, such as a battery handle and lamp, and includes a bundle of optical fibers that transmits light from the lamp to the distal end of the needle. A flexible catheter is releasably mounted on the needle and is adapted to be inserted in the vein after the needle has punctured it. Thereafter, the needle can be withdrawn from the catheter and the latter taped in position.

BRIEF DESCRIPTION OF THE DRAWINGS

FIG. 1 is a perspective view of a battery handle and hypodermic needle embodying the invention;

FIG. 2 is an enlarged, fragmentary side elevation of the handle and needle of FIG. 1 with parts shown in section to illustrate the details of construction;

FIG. 3 is an enlarged longitudinal section through the needle;

FIG. 4 is a transverse section through the needle taken on line 4—4 of FIG. 3; and FIG. 5 is a transverse section corresponding to FIG. 4 but showing a modification of the configuration of the fiber optic bundle.

DESCRIPTION OF THE PREFERRED EMBODIMENTS

Having reference now to the drawings, 10 generally indicates a battery handle to which a needle-catheter assembly, generally indicated at 11, is releasably attached. Battery handle 10 is substantially conventional and comprises a cylindrical case 12 in which two or more batteries 14 are positioned, the case having a removable bottom cap 15 and the usual on-off switch 16. A sleeve 17, FIG. 2, is fixed in the top wall 18 of the battery handle case and this sleeve supports an inner sleeve 20 in which a lamp 21 is received with a friction fit, the lower terminal of the lamp engaging a battery terminal as shown.

The needle-catheter assembly 11 includes a tubular needle 22 the proximal end of which is fixed in a hub member 24. The hub member is releasably connected to the battery handle sleeve 17 by any suitable means such as a bayonet type fastening 25, FIG. 1. A generally cylindrical bundle of optical fibers 26 is fixed in position in the interior of needle 22 as best shown in FIGS. 3 and 4, the diameter of the bundle being substantially less than the inner diameter of the needle as indicated.

At the proximal end of the needle, the fiber optic bundle 26 projects outwardly so as to be positioned close to, and in alignment with, the filament of lamp 21 as shown in FIG. 2. The bundle extends the full length of the needle and at the distal end thereof its light emitting end 27 is slanted to conform to the slanted puncturing end 28 of the needle. Both ends of the fiber optic bundle are ground and polished whereby the bundle receives light from the lamp and transmits it to the distal end of the needle with substantially no light loss.

As indicated in FIG. 5, the fiber optic bundle 26a could, alternatively, have an annular configuration concentric with the needle 22, the construction otherwise being the same.

Releasably mounted on the needle 22 is a flexible, tubular catheter 30 of conventional construction. At its proximal end, the catheter has a standard size hub 31 for attachment to intervenous tubing (not shown), the hub 31 fitting over a reduced diameter portion 32 of the needle hub member 24. The distal end of catheter 30 stops short of the distal end of needle 22 so that the latter is exposed for the venopuncture, and the catheter end is rounded at 34, FIG. 2, so that it will not perforate or damage the vein.

In using the hypodermic needle of the invention to puncture a vein in the arm, for example, the usual tourniquet is applied and the arm cleansed. The battery handle lamp 21 is then turned on to illuminate the distal end of the needle 22 which is inserted in the arm near the target vein. The light at the distal end of the needle enables it to be seen through the skin and facilitates guiding it to the vein which it penetrates. Reflux of blood back through the needle indicates that it is in correct position. After the needle tip has penetrated the vein, the catheter is pushed along the needle to cause its rounded end 34 to enter the vein. The catheter can then be taped in place, the needle withdrawn and the catheter hub attached to intervenous tubing.

From the foregoing description it will be apparent that the invention provides a novel and very beneficial illuminated hypodermic needle. As will be apparent to those familiar with the art, the invention may be embodied in other specific forms without departing from the spirit or essential characteristics thereof.

I claim:

1. A hypodermic needle assembly comprising in combination a portable light source, a hypodermic needle releasably connected at its proximal end to the light source, the needle being adapted to emit light at its distal end to facilitate venopuncture under subdued lighting conditions, the emitted light making it easier to locate and penetrate the vein, a bundle of light conducting optical fibers positioned in the interior of the needle and extending from adjacent the proximal to adjacent the distal end thereof, the bundle having a light receiving face at its proximal end for receiving light from the light source and having a light emitting face at its distal end for illuminating the distal end of the needle, the bundle occupying a portion only of the interior of the needle whereby an unoccupied longitudinal passage remains for the flow of blood from the distal back to the proximal end of the needle after penetration of the vein, and a flexible catheter releasably mounted on the needle and extending from a point adjacent its proximal to a point adjacent its distal end, the catheter being adapted to enter the vein after the distal end of the needle has punctured same after which the needle can be withdrawn from the catheter.

2. A needle assembly as defined in claim 1 wherein the light source is a lamp supported by a battery handle.

3. A needle assembly as defined in claim 1 wherein the bundle of optical fibers has a substantially circular cross section.

4. A needle assembly as defined in claim 1 wherein the bundle of optical fibers has a substantially annular cross section.

* * * * *